United States Patent [19]
Perez et al.

[11] Patent Number: 6,132,448
[45] Date of Patent: Oct. 17, 2000

[54] ENDOSCOPIC IRRIGATED BUR

[75] Inventors: Juan I. Perez, San Jose; Barry J. Kauker, Soquel, both of Calif.

[73] Assignee: Stryker Corporation, Kalamazoo, Mich.

[21] Appl. No.: 09/100,593

[22] Filed: Jun. 19, 1998

[51] Int. Cl.[7] .............................. A61B 17/14; A61B 17/32
[52] U.S. Cl. ............................................................. 606/180
[58] Field of Search ................................ 606/159, 168, 606/169, 170, 171, 179, 180; 604/22

[56] References Cited

U.S. PATENT DOCUMENTS

| | | | |
|---|---|---|---|
| 3,937,222 | 2/1976 | Banko | 606/170 |
| 4,167,944 | 9/1979 | Banko | 606/170 |
| 4,643,717 | 2/1987 | Cook et al. | 606/169 |
| 4,842,578 | 6/1989 | Johnson et al. | |
| 5,019,036 | 5/1991 | Stahl | 606/170 |
| 5,041,082 | 8/1991 | Shiber | 606/159 |
| 5,507,292 | 4/1996 | Jang et al. | 606/159 |
| 5,514,115 | 5/1996 | Frantzen et al. | 606/159 |
| 5,569,284 | 10/1996 | Young et al. | 606/170 |
| 5,618,293 | 4/1997 | Sample et al. | 606/170 |
| 5,632,759 | 5/1997 | Rexroth | |
| 5,741,287 | 4/1998 | Alden et al. | 606/170 |
| 5,792,167 | 8/1998 | Kablik et al. | 606/170 |

FOREIGN PATENT DOCUMENTS 0 190 000  8/1986  European Pat. Off. .

*Primary Examiner*—Gene Mancene
*Assistant Examiner*—Eduardo C. Robert
*Attorney, Agent, or Firm*—Flynn, Thiel, Boutell & Tanis, P.C.

[57] ABSTRACT

A cutting blade assembly for use with a handpiece having a motor for rotatably driving the cutting blade assembly. The handpiece has a bore therein for receiving the cutting blade assembly. The cutting blade assembly includes an elongate tubular outer member having a distal end with an opening thereat, a proximal end, a hub unremovably secured to the proximal end so as to be a permanent part of the outer member. The hub is configured to be directly received and engaged in the handpiece bore. An elongate inner member is received in the outer member and has a distal cutting end disposed adjacent the opening in the distal end of the outer member. A proximal end of the inner member is adapted to be received in the handpiece bore and rotatably driven by the motor to rotate the inner member in the outer member. The cutting blade assembly includes the elongate tubular outer member having a radially inwardly facing surface along the length thereof with at least one elongate axially extending groove therein, the groove terminating at both the proximal and distal ends of the outer member. The cutting blade assembly also includes the outer member additionally having an irrigation liquid connection structure and a window through a wall of the outer member for providing liquid communication between the liquid connection structure and the elongate axially extending groove so that liquid will traverse the axial extent of the groove and to the opening. Bearings relatively rotatably support the inner and outer members and the irrigation liquid bypasses the bearings through the groove.

18 Claims, 7 Drawing Sheets

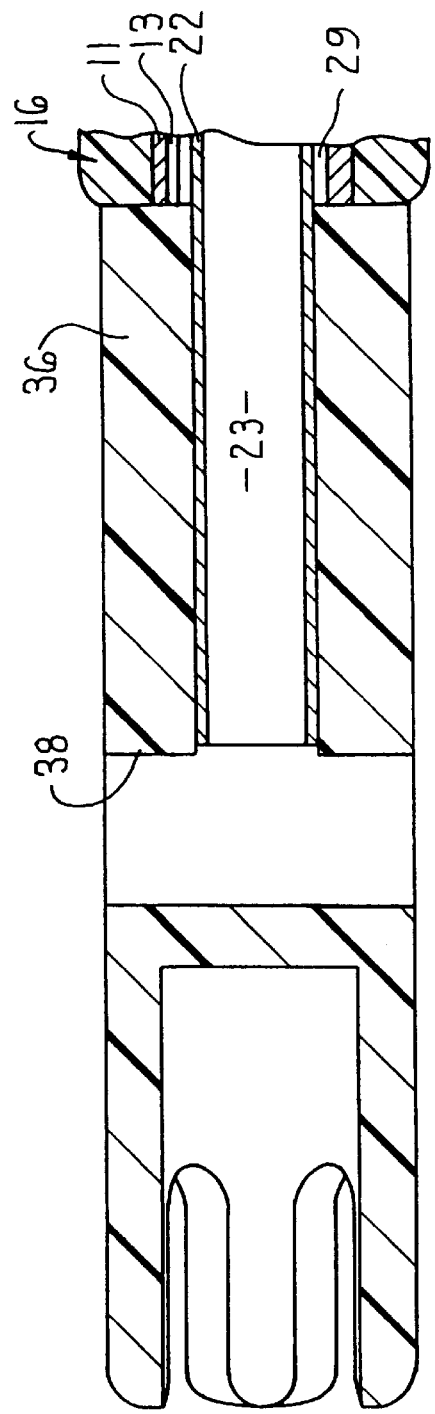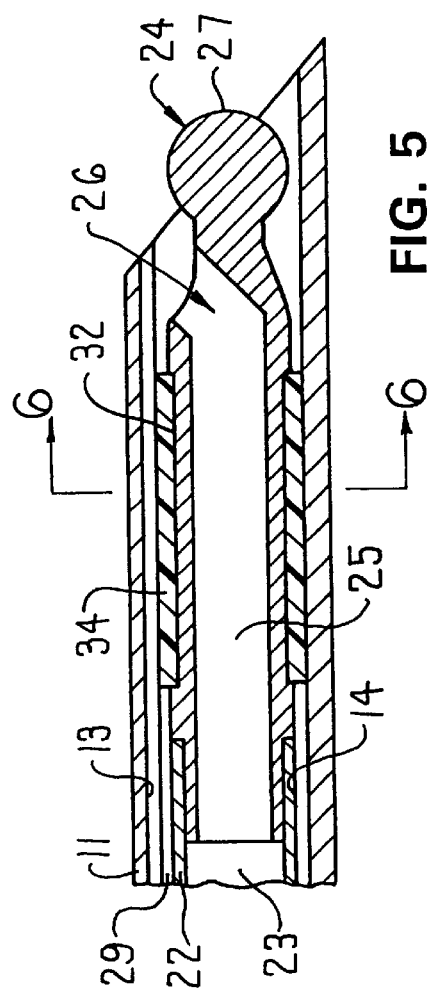

ENDOSCOPIC IRRIGATED BUR

CROSS-REFERENCE TO RELATED APPLICATION

This application is related to pending application Ser. No. 08/713,434, filed Sep. 13, 1996.

FIELD OF THE INVENTION

This invention relates to an improved surgical tool for use in a surgical irrigation pump and tool system of the type disclosed in U.S. Pat. No. 5,792,167 issued Aug. 11, 1998.

BACKGROUND OF THE INVENTION

Pending application Ser. No. 08/713,434, filed Sep. 13, 1996, discloses an irrigation surgical tool system which includes a motorized handpiece, a surgical tool removably insertable therein, a console including a peristaltic pump rotor and a tube set including a cassette mountable on the console for coaction with the rotor to supply irrigation liquid to the tool. The teachings in the aforesaid pending application are to be incorporated herein by reference.

An irrigation liquid passageway exists on the tool between the elongate tubular outer member and the elongate tubular inner member to facilitate the passage of liquid between the tubes to the surgical site. Since the elongate inner tubular member is driven at a very high speed of rotation, it is desirable to support the elongate inner tubular member inside the elongate outer tubular member by bearings. The provision of bearings will restrict the flow of irrigation liquid in the aforesaid passageway. Accordingly, it is desirable to provide a structure for enhancing the flow of irrigation liquid to the surgical site and between the elongate inner and outer tubular members.

SUMMARY OF THE INVENTION

The objects and purposes of the invention are met by providing an improved surgical tool for use with a handpiece, the handpiece having a motor for rotatably driving the surgical tool, the handpiece having a bore therein for receiving the surgical tool. The surgical tool includes an elongate tubular outer member having a distal end with an opening thereat, a proximal end, a hub unremovably secured to the proximal end so as to be a permanent part of the outer member, the hub being configured to be directly received and engaged in the handpiece bore. An elongate inner member is received in the outer member and has a distal cutting end disposed adjacent the opening in the distal end of the outer member. A proximal end of the inner member is adapted to be received in the handpiece bore and rotatably driven by the motor to rotate the inner member in the outer member. The improved surgical tool includes the elongate tubular outer member having a radially inwardly facing surface along the length thereof and having at least one elongate axially extending groove in the radially inwardly facing surface, the groove terminating at both the proximal and distal ends of the outer member. The improvement also includes the outer member additionally having an irrigation liquid connection structure and a window through a wall of the outer member for providing liquid communication between the liquid connection structure and the elongate axially extending groove so that liquid will traverse the axial extent of the groove and to the opening.

BRIEF DESCRIPTION OF THE DRAWINGS

Other objects and purposes of the invention will become apparent to persons skilled in this art upon a reading of the following specification with reference to the accompanying drawings, in which:

FIG. 3 is an enlarged fragment of the left end of FIG. 2;

FIG. 5 is an enlarged fragment of the right end of the tool illustrated in FIG. 2;

DETAILED DESCRIPTION

Figure 1:
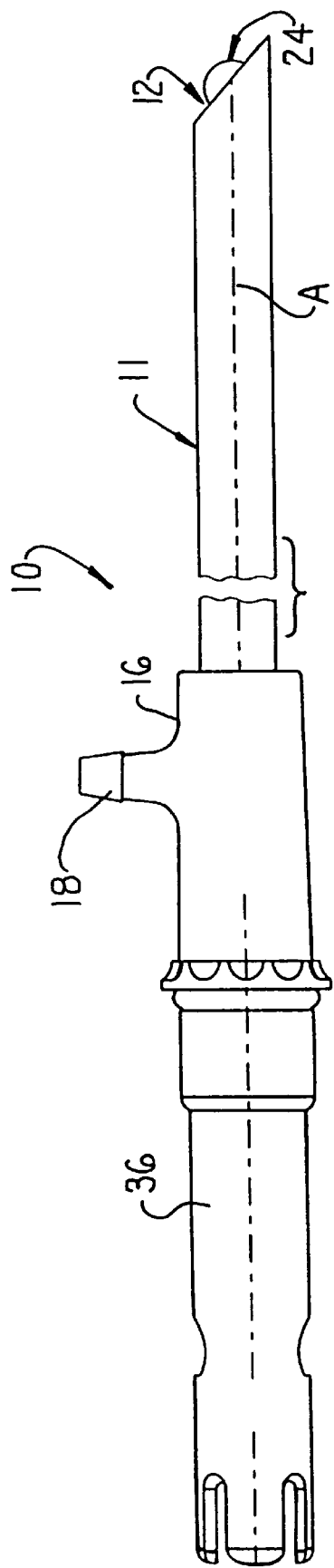
FIG. 1 is a side elevational view of a surgical tool embodying the invention.
Figure 6:
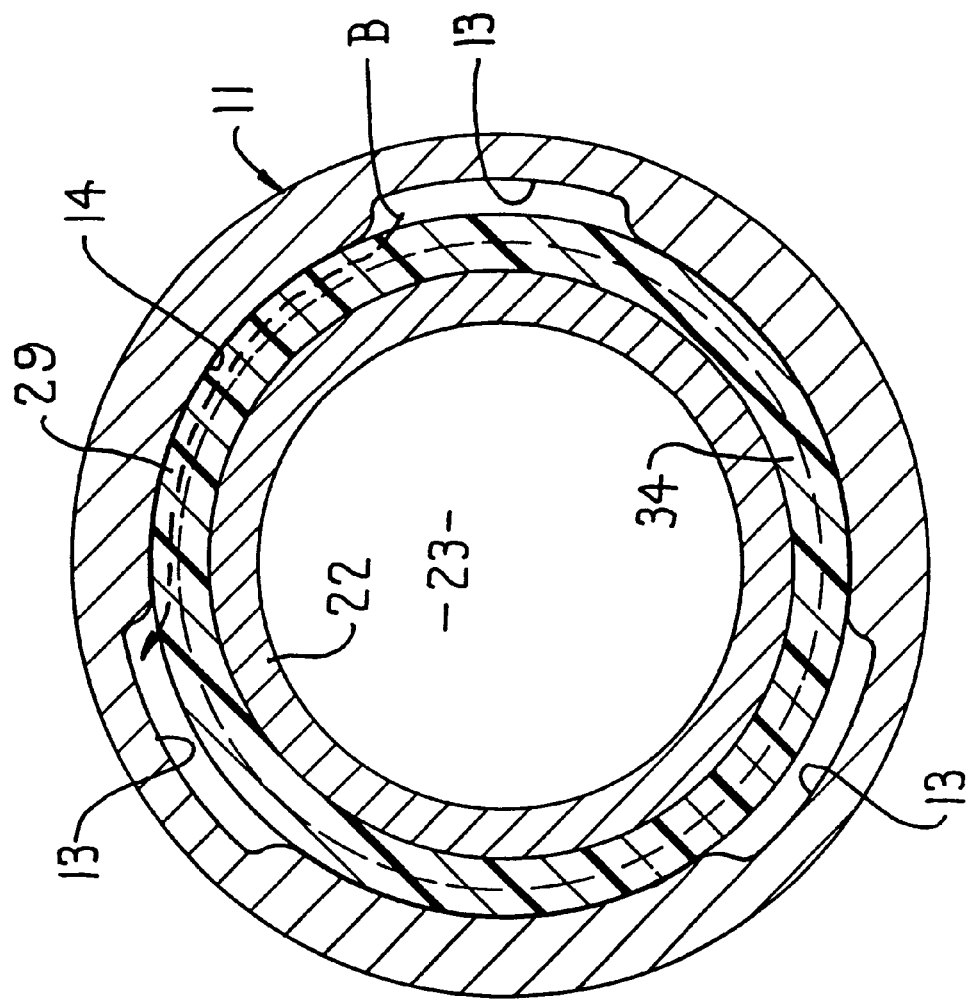
FIG. 6 is a sectional view taken along the line 6—6 of FIG. 5.

FIG. 1 illustrates a surgical tool 10 embodying the invention. The surgical tool includes an elongate tubular outer member 11 opening outwardly as at 12 at the right or distal end thereof. The outer member 11 is an extruded member made of stainless steel. The right end of the outer member 11 is cut in a plane that is oriented at about a 45° angle to the longitudinal axis A of the tool. The left end of the outer member 11 is cut in a plane that is generally perpendicular to the aforesaid longitudinal axis A. As is illustrated in FIG. 6, several, here three, elongated grooves 13 are provided in a radially inwardly facing surface 14 of the outer member 11, the grooves extending parallel to one another and axially along the full length of the outer member 11. The grooves 13 are of a finite depth in the wall thickness of the outer member 11. In this particular embodiment, the grooves 13 are equidistantly spaced from one another. The purpose of these grooves will be explained in more detail below.

The left end of the outer member 11 has a plastic housing hub 16 unremovably secured to the proximal end so as to be a permanent part of the outer member. In this particular embodiment, the housing hub 16 is made of a polycarbonate material. The housing hub is configured to be directly received and engaged in a handpiece bore 17 illustrated in FIG. 8. In this particular embodiment, the housing hub 16 is similar in many respects to the hub on the tool illustrated in U.S. Pat. No. 5,792,167 issued Aug. 11, 1998. That is, the housing hub 16 includes an irrigation liquid connection 18 having a liquid passageway 19 extending in a generally radial direction of the tool 10. A window opening 21 is provided through the wall of the outer member 11 so that liquid can communicate from the irrigation liquid connection 18 to the interior of the outer member 11.

Figure 7:
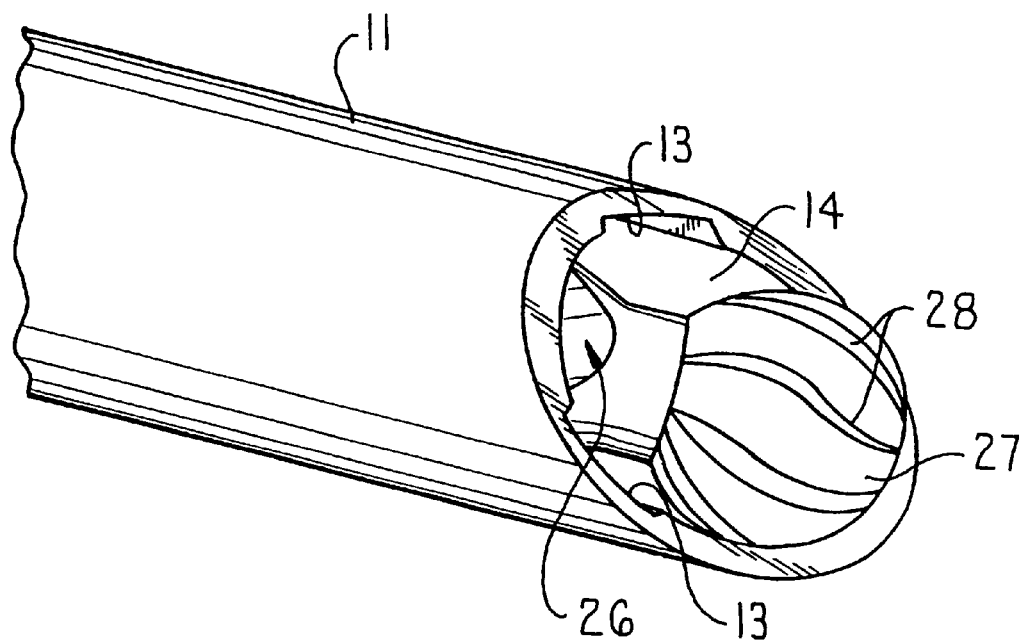
FIG. 7 is an enlarged isometric view of the right end portion of the tool illustrated in FIG. 2.

An elongate tubular inner member 22 is received inside the outer member 11. The elongate inner member 22 has a hollow interior 23 extending lengthwise thereof. A cutting tool 24 is secured to the distal end of the inner member 22 as illustrated in FIG. 5. In this particular embodiment, the tool 24 is hollow and has a central passageway 25 therethrough communicating with the interior 23 of the inner member 22. The distal end of the passageway 25 terminates in an opening 26 oriented adjacent a cutting tip 27 at the distal end of the cutting tool 24. The cutting tip 27 is, in this particular embodiment, a ball-shaped implement, or bur, as illustrated in FIG. 7 having a plurality of sharp cutting flutes or edges 28 extending circumferentially on the surface of the ball.

Figure 4:
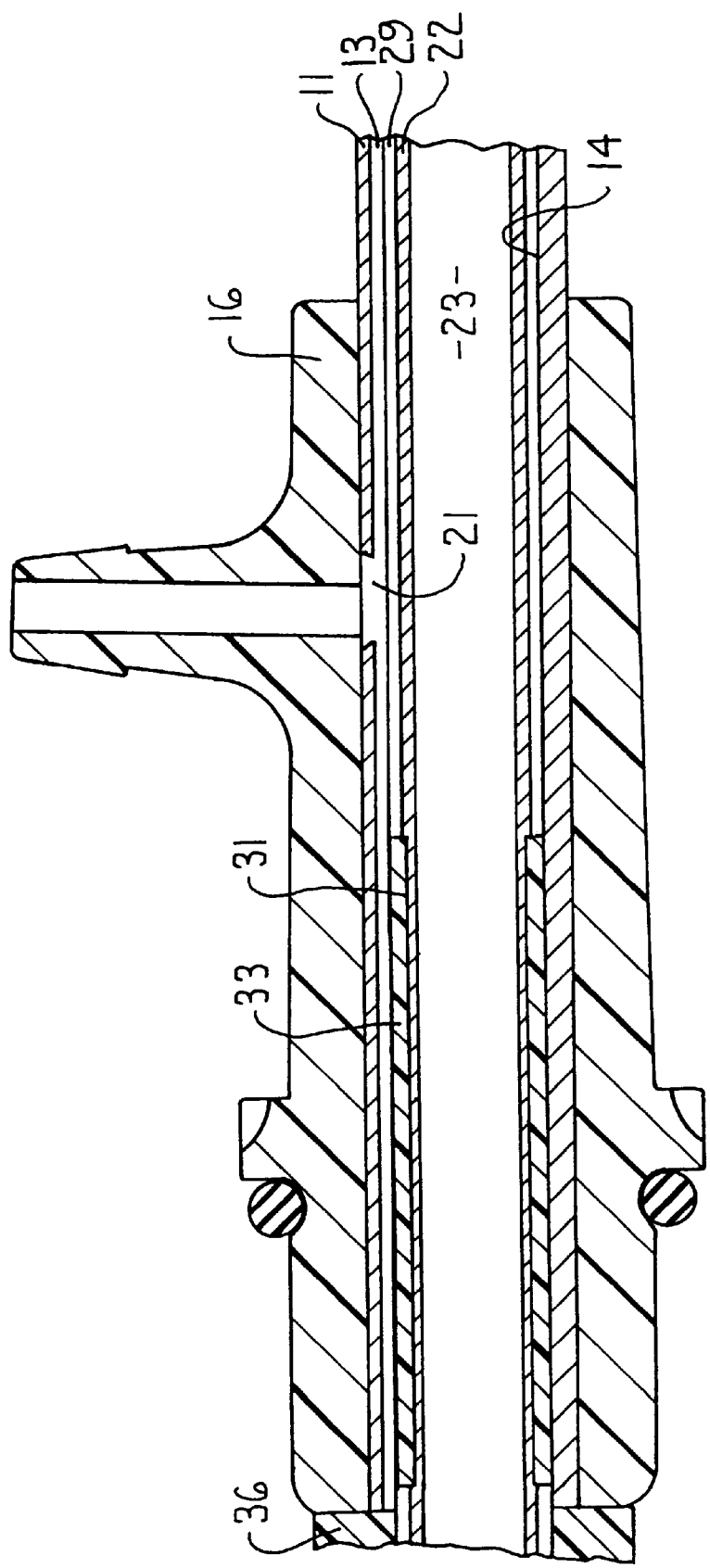
FIG. 4 is an enlarged fragment of a central region of FIG. 2.

As shown in FIG. 4, the outer diameter of the inner member 22 is smaller than the diameter of the radially inwardly facing surface 14 of the outer member 11 so as to define a gap 29 therebetween. Reduced diameter sections 31 and 32 are provided in the outer surface of each of the inner member 22 and the cutting tool 24, respectively, and as best shown in FIGS. 4 and 5. These reduced diameter sections 31 and 32 each receive therein a cylindrical fluorinated ethylene propylene (FEP) plastic bearing sleeve 33 and 34, the radially outwardly facing surface of the Teflon bearing sleeves 33 and 34 snugly engaging the radially inwardly facing surface 14 so as to rotatably support the inner member 22 and tool 24 inside the outer member 11.

The proximal end of the inner member 22 (FIG. 8) has a glass/Teflon filled polycarbonate hub 36 unremovably secured to the proximal end of the inner member 22 so as to be a permanent part of the inner member. The hub 36 is configured to be directly received and engaged in the handpiece bore 17 and rotatably driven by the output shaft 37 (FIG. 8) of the motor oriented inside the handpiece. The hub 36 has a passageway 38 extending radially therethrough and communicates with the interior 23 of the inner member 22 as illustrated in FIG. 3. If desired, the hub 36 can be secured to the inner member 22 as by an adhesive or by inductive welding (not illustrated).

Figure 2:
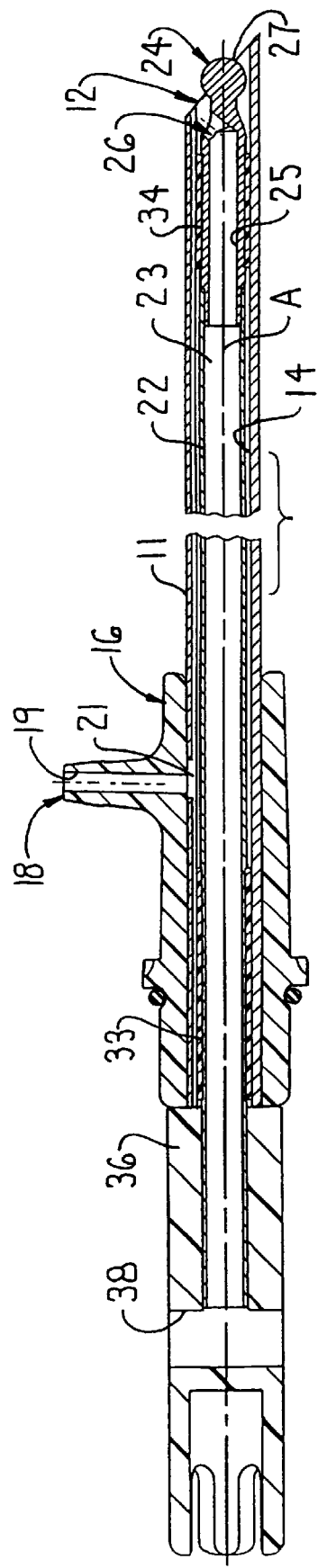
FIG. 2 is a central sectional view of the tool illustrated in FIG. 1.
Figure 8:
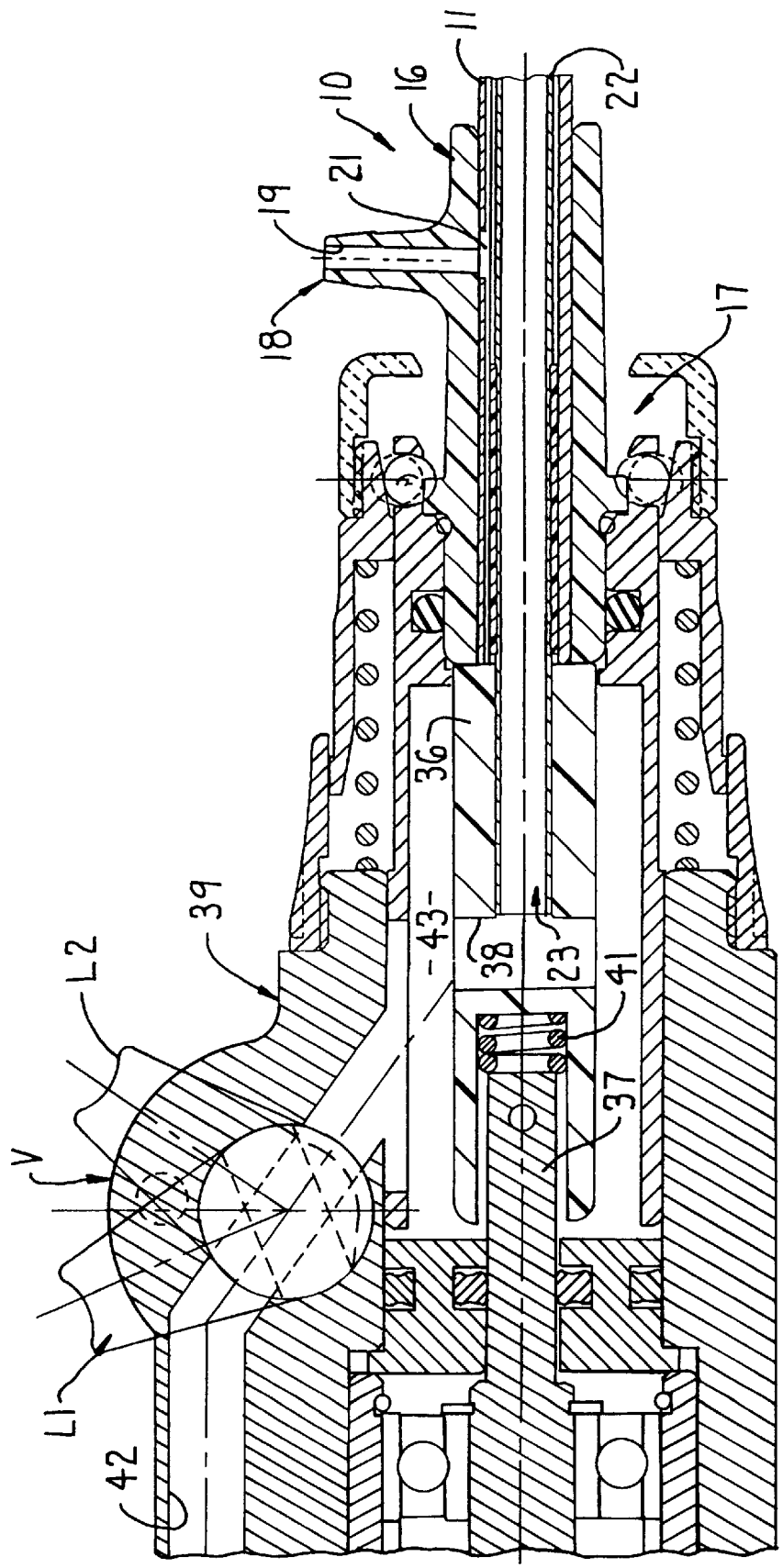
FIG. 8 is a sectional view of the left end portion of the tool coupled to a handpiece having a drive motor therein.

In use, the tool is adapted to be coupled to the handpiece 39 illustrated in FIG. 8 in virtually the same manner as is the tool, particularly the housing hub 16, coupled to the handpiece and taught in the U.S. Pat. No. 5,792,167. Thus, further discussion concerning the manner in which the tool, particularly the outer member 11, is secured to the handpiece is believed unnecessary. However, when the tool 24 is engaged, it will be apparent that a spring 41 oriented between the drive shaft 37 of the motor inside the handpiece 39 and the hub 36 will urge the hub 36 into engagement with the proximal end of the hub 16 on the outer member 11. The structure by which the housing hub 16 is secured to the handpiece 39 holds the outer member 11 and housing hub 16 secured thereto stationary while the hub 36 and the inner member 22 are rotatable. Irrigation liquid is supplied to the passageway 19 (FIG. 4) in the irrigation liquid connection 18 and is allowed to pass through the window opening 21 in the outer member 11 into the gap 29 between the outer surface of the inner member 22 and the inner surface 14 of the outer member 11. The irrigation liquid will flow along the path of least resistance (FIG. 2), namely, toward the distal end of the outer member 11 and the opening 12 thereat. The bearing sleeves 33 and 34 which rotatably support the inner member 22 and cutting tool 24 inside the outer member 11 would tend to block the flow of irrigation liquid toward the distal end and the opening 12 thereat were it not for the plural elongated grooves 13 (FIG. 6) in the inside surface 14 of the outer member 11. That is, the irrigation liquid will flow through the gap 29 into the respective grooves 13 as indicated by the arrow B in FIG. 6. The flow of liquid toward the proximal end of the outer member 11, namely, to the left in FIG. 4 will be resisted by the abutting axially facing end surface of the hub 36 with an oppositely facing end surface of the hub 16.

The inner member 22 and the hub 36 secured thereto are rotated at a very high speed, namely, in the range of 6,000 rpm relative to the stationary hub 16 and outer member 11 secured thereto. Since the interfacing and engaged axially facing surfaces on the hub 36 and the hub 16 frictionally contact one another, the heat generated by the friction will promote the glass/Teflon filled polycarbonate material of the hub 36 to provide an appropriate self lubrication therebetween.

When it is desired to remove the irrigation liquid from the surgical site, a valve V (FIG. 8) on the handpiece 39 can be opened by moving a lever L from the position L1 to the position L2 so as to connect a suction source connected in circuit with the passageway 42 in the handpiece 39 through the valve V to an annular chamber 43 which communicates with the passageway 38 in the hub 36. Such connection will provide communication between the interior 23 of the inner member 22 and the suction source so as to cause irrigation liquid to flow into the opening 26 (FIG. 2) adjacent the tool tip 27 and pass through the connected passageways 23 and 25 to the passageway 42 in the handpiece 39.

Although a particular preferred embodiment of the invention has been disclosed in detail for illustrative purposes, it will be recognized that variations or modifications of the disclosed apparatus, including the rearrangement of parts, lie within the scope of the present invention. For example, the phrase "surgical tool" is to be interpreted to mean both a cutting blade assembly as well as the disclosed bur.

The embodiments of the invention in which an exclusive property or privilege is claimed are defined as follows:

1. A disposable, limited use surgical tool for use with a powered handpiece with motor means for rotatably driving said surgical tool, the handpiece having a housing and bore means therein for receiving said surgical tool, said surgical tool comprising:

an elongate tubular outer member having a distal end with an opening thereat, a proximal end, a proximal end hub secured to the proximal end so as to be a permanent part of said outer member, said hub being configured to be directly received and engaged in said handpiece bore means and to said housing;

an elongate inner member received in said outer member and having a distal end disposed adjacent said opening in said distal end of said outer member, and a proximal end adapted to be received in the handpiece bore means and rotatably driven by the motor means to rotate said inner member in said outer member;

an improvement wherein said elongate tubular outer member has a radially inwardly facing surface having along a length thereof at least one elongate axially extending groove therein, said at least one elongate axially extending groove terminating at said proximal and distal ends of said elongate tubular outer member; and wherein said hub on said elongate tubular outer member includes means defining an irrigation liquid connection means, and wherein a window is provided through a wall of said elongate tubular outer member for providing liquid communication between said liquid connection means and said at least one elongate axially extending groove so that liquid will traverse the axial extent of said elongate axially extending groove and to said opening.

2. The surgical tool according to claim 1, wherein said inwardly facing surface has at least three equidistantly spaced axially extending and parallel grooves therein, each of said grooves terminating at said proximal and distal ends of said elongate tubular outer member.

3. The surgical tool according to claim 1, wherein said elongate tubular outer member is an extrusion.

4. The surgical tool according to claim 1, wherein said elongate tubular outer member is machined.

5. The surgical tool according to claim 1, wherein said elongate inner member has a suction passageway extending longitudinally therethrough, said suction passage extending between said proximal end hub and said distal end, said suction passageway adapted to be connected to a source of suction, said suction passageway terminating at a suction port adjacent said inner distal cutting end, said suction port operable to remove tissue particles and the irrigation fluid from a surgical site.

6. The surgical tool according to claim 1, wherein said groove has a depth less than the wall thickness of said elongate tubular outer member.

7. The surgical tool according to claim 1, wherein said elongate inner member is supported by spaced bearing means axially fixed between said elongate inner and tubular outer members for supporting said elongate inner member at a constant radial distance from said radially inwardly facing surface of said elongate tubular outer member.

8. The surgical tool according to claim 7, wherein said at least one axially extending groove provides a flow path for the irrigation fluid to flow past said bearing means.

9. The surgical tool according to claim 7, wherein said spaced bearing means are each a fluorinated ethylene propylene plastic sleeve axially spaced along the length of, and between, said elongate inner and tubular outer members.

10. The surgical tool according to claim 7, wherein said elongate inner member includes a reduced diameter section in an outer surface of said inner member and receives one of said bearing means thereat, said bearing means comprising a plastic bearing sleeve.

11. The surgical tool according to claim 1, wherein said proximal end hub is made of a glass/Teflon filled polycarbonate material and said irrigation liquid connection means is made from a polycarbonate material, so that during operation of said surgical tool, said proximal end hub rotates against said irrigation liquid connection means such that frictional heat is generated between said proximal end hub and said irrigation liquid connection means, said polycarbonate material operable in response to said frictional heat to promote self lubrication between said irrigation liquid connection means and said proximal end hub.

12. The surgical tool according to claim 1, wherein said irrigation liquid connection means and said proximal end hub are connectable to a rotatable shaft of said motor means in said powered rotating handpiece to cause relative rotation between said elongate tubular outer member and said elongate inner member.

13. A surgical tool for use with a powered handpiece having motor means for rotatably driving said surgical tool, the handpiece having a housing and bore means therein for receiving said surgical tool, said surgical tool comprising:

an elongate tubular outer member having a proximal end and a distal end with an opening thereat, a proximal end hub secured to the proximal end of said tubular outer member so as to be a permanent part of said outer member, said hub being configured to be directly received and engaged in the bore means of the handpiece;

a rotatable elongate inner member received in said tubular outer member and having a distal cutting end disposed adjacent said opening in said distal end of said outer member, and a proximal end adapted to be received in the bore means and rotatably driven by the motor means to rotate said inner member in said outer member;

an improvement wherein said elongate tubular outer member has a radially inwardly facing surface and has a length defining a longitudinal axis thereof, at least one elongate axially extending groove therein extending the length thereof, said at least one elongate axially extending groove terminating at said proximal and distal ends of said elongate axially extending elongate tubular outer member; and wherein said at least one elongate axially extending groove enables application of irrigation liquid.

14. A surgical tool for use with a powered handpiece having motor means for rotatably driving said surgical tool, the handpiece having a housing and bore means therein for receiving said surgical tool, said surgical tool comprising:

an elongate tubular outer member having a proximal end and a distal end with an opening thereat, the distal end defining a plane, said elongate tubular outer member having a radially inwardly facing surface including at least one elongate axially extending groove extending along a length of the inwardly facing surface, said at least one elongate axially extending groove terminating at the distal end of said elongate tubular outer member;

a hub secured to the proximal end of said elongate tubular outer member, said hub configured to be received and engaged in the bore means;

an elongate inner member received in said tubular outer member and having a distal end disposed adjacent said opening in said distal end of said tubular outer member and a proximal end adapted to be received in the bore means and rotably driven by the motor means;

a bearing sleeve secured to said elongate inner member; and a cutting tip secured to the distal end of said elongate inner member.

15. The surgical tool according to claim 14, wherein said cutting tip protrudes outwardly beyond the plane at the distal end of said elongate tubular outer member.

16. The surgical tool according to claim 14, wherein a reduced diameter section in an outer surface of said cutting tip receives a second bearing sleeve axially spaced from the first bearing sleeve.

17. The surgical tool according to claim 14, wherein said cutting tip comprises a bur.

18. The surgical tool according to claim 14, wherein said cutting tip comprises a ball-shaped implement having a plurality of cutting flutes extending circumferentially on a surface of said implement.

* * * * *